United States Patent [19]

Waite et al.

[11] Patent Number: 5,869,459
[45] Date of Patent: Feb. 9, 1999

[54] FROZEN REHYDRATION FORMULATION AND DELIVERY SYSTEM THEREFOR

[75] Inventors: Christopher S. Waite, Cary, Ill.; R. Douglas Frix, Bluffdale, Utah

[73] Assignee: PTS Labs LLC, Deerfield, Ill.

[21] Appl. No.: 786,072

[22] Filed: Feb. 10, 1997

Related U.S. Application Data

[63] Continuation of Ser. No. 323,229, Oct. 14, 1994, abandoned.

[51] Int. Cl.⁶ .................................................. A61K 31/70
[52] U.S. Cl. ................................. 514/23; 514/25; 514/53; 424/400; 426/76; 426/100; 426/103
[58] Field of Search .................................. 514/25, 53, 23; 424/400; 426/76, 100, 103

[56] References Cited

U.S. PATENT DOCUMENTS

| | | |
|---|---|---|
| 4,450,170 | 5/1984 | Beeley et al. . |
| 4,505,926 | 3/1985 | Newsome et al. . |
| 4,520,014 | 5/1985 | Newsome et al. . |
| 4,539,319 | 9/1985 | Newsome et al. . |
| 4,558,063 | 12/1985 | Beeley et al. . |
| 4,594,195 | 6/1986 | Newsome et al. . |
| 4,942,042 | 7/1990 | Bharagava et al. . |
| 5,096,894 | 3/1992 | Tao et al. ................................... 514/58 |
| 5,192,551 | 3/1993 | Willoughby et al. . |
| 5,270,297 | 12/1993 | Paul et al. ................................. 514/23 |
| 5,290,605 | 3/1994 | Shapira . |
| 5,292,538 | 3/1994 | Paul et al. ................................. 426/74 |
| 5,431,915 | 7/1995 | Harvey et al. ........................... 424/439 |

*Primary Examiner*—Elli Peselev
*Attorney, Agent, or Firm*—McDonnell, Boehnen, Hulbert & Berghoff

[57] ABSTRACT

A rehydrating freezer pop provides a convenient and effective way of replenishing lost fluid and electrolytes. The frozen formulation masks unpleasant tastes of electrolyte and is readily consumed children.

4 Claims, No Drawings

FROZEN REHYDRATION FORMULATION AND DELIVERY SYSTEM THEREFOR

This application is a file wrapper continuation of application Ser. No. 08/323,229 filed Oct. 14, 1994, now abandoned.

BACKGROUND OF THE INVENTION

1. Field of the Invention

The invention is directed to a rehydration formulation for the replacement of electrolytes and enhanced water retention. In particular, the invention relates to a frozen rehydration formulation and unique delivery system therefor. The delivery system provides a convenient and effective vehicle for administering therapeutic agents in a way that is readily acceptable to children.

2. Description of Related Art

It is known that both negative energy balance and muscle catabolism are consequences of physiological stress that often accompanies protein calorie malnutrition, strenuous physical exercise, physical trauma, burn injury, surgical trauma, malnutrition, maldigestion, malabsorption, hyperthyroidism, chemotherapy, radiation therapy, anorexia, cachexia, short bowel syndrome, old age, and sepsis. It is also known that maintaining a positive metabolic energy balance can help to alleviate such problems and also has a sparing effect on muscle catabolism that occurs during strenuous physical exertion.

In order to properly combat the symptoms of physiological stress, it is essential that appropriate amounts of nutrients be available to replace those which are utilized or lost. Proper food energy (available calories), hydration and mineral bioavailability are essential to enable the body to maintain a proper balance in both intracellular and extracellular fluids and to also maintain proper enzymatic functioning, pH balance, osmotic pressure, and the like.

Nutritional supplements including liquid endurance and rehydration compositions are well known in the art. Rehydration solutions are conventionally used to replace electrolytes lost during vomiting and diarrhea, as well as during strenuous exercise. Diarrhea in particular can be a severe disease, especially in infants and young children, and can often result in death. Diarrhea is common amongst travellers and those exposed to low standards of hygiene. Diarrhea frequently involves colonization of the small intestine with enteropathogenic strains of E. coli which produce heat stable and/or heat labile enterotoxins. Related enterotoxins are produced by other enteropathogens such as cholera, and also cause diarrhea. These enterotoxins stimulate fluid secretion in the gut lumen and cause diarrhea. Associated fluid loss may lead to death.

In cases of severe dehydration corrective parenteral therapy is often necessary. In cases of mild to moderate dehydration oral rehydration solutions provide a safe, economical alternative to intravenous therapy. In order to promote rehydration, it is necessary to provide a source of energy and also a source of dietary supplements which can be directed to proper cellular and/or tissue sites in the course of the rehydration process. Oral rehydration solutions used in oral rehydration therapy generally consist of a mixture of electrolytes and a carbohydrate component such as glucose or sucrose. Examples of commercially available oral electrolyte replacement and/or maintenance solutions include Rehydrolyte® and Pedialyte®, manufactured by Ross Laboratories, Columbus, Ohio, and Magonate® Liquid, manufactured by Fleming and Company, Fenton, Mo.

The development of oral rehydration therapy for acute diarrheal diseases of infancy and childhood has significantly reduced related morbidity and mortality, particularly in less developed countries where it constitutes the primary mode of therapy. The World Health Organization (WHO) currently recommends that oral rehydration solutions for treatment of acute diarrheal therapy contain 90 mEq sodium/liter, 20 mEq potassium/liter, 80 mEq chloride/liter, 30 mEq citrate/liter or 30 mEq bicarbonate/liter, and 110 mmol glucose/liter. Glucose is recommended as the carbohydrate component in such oral rehydration solutions. Glucose enhances the membrane transport of sodium which in turn enables rapid uptake of water. The WHO formulation has been shown to decrease morbidity and mortality.

Substitution of other carbohydrates for glucose in WHO-type formulations has been investigated. Lebenthal et al. (*J. Pediatrics,* 1983, 103:29–34) studied the effect of three corn syrup sugars (dextrins) containing glucose polymers of varying lengths having dextrose equivalents of 10, 15 and 24 and determined they were suitable as the sole carbohydrate source in oral rehydration therapy. It has also been established that oral rehydration solutions in which rice and other food sources of starch are substituted for glucose are effective as reported by Carpenter et al. (*New England J. Med.,* 1988, 319:1346–1348). Rice-based oral rehydration solutions containing from 3 to 5% rice and having electrolyte levels corresponding to conventional WHO formulations, have been found to be effective as reported by Patra et al. (*Archives of Disease in Childhood,* 1982, 57:910–912), Molla et al. (*The Lancet,* 1982, pp. 1317–1319), El Mougi et al. (*Journal of Pediatric Gastroenterology and Nutrition,* 1988, 7:572–576), and Molla et al. (*Journal of Gastroenterology and Nutrition,* 1989, 8:81–84). U.S. Pat. No. 5,096,894 discloses an oral rehydration solution comprising a mixture of the required electrolytes and rice dextrin containing a distribution of short chain glucose polymers consisting of 50–90% 2 to 6 glucose units.

U.S. Pat. No. 5,270,297 discloses an oral rehydration solution including a blend of simple sugars, more complex carbohydrates and minerals, in particular magnesium. Other ingredients include electrolyte ions (e.g., potassium, sodium, chloride), vitamins, anabolic nutrients, and other minerals such as calcium. The magnesium and calcium are provided in the form of amino acid chelates to facilitate rehydration and promote endurance.

U.S. Pat. Nos. 4,505,926, 4,539,319, 4,558,063 and 4,594,195 disclose various oral rehydration solutions containing pharmaceutically active ingredients (i.e., drugs) for treatment of enterotoxin induced diarrhea and prevention of death from enteropathogenic E. coli infection of the gastrointestinal tract. Drugs incorporated into these prior art rehydration solutions include quaternary aminophenyliminoimidazolidines, 2-aminoimidazoline derivative, and 5,6,7,8-tetrahydro-naphonitrile intermediates.

U.S. Pat. No. 4,942,042 is directed to an anti-diarrhea composition comprising an absorptive component and an electrolyte/sugar component. The absorptive material is a thermally activated, finely powdered, hydrous magnesium aluminum silicate clay capable of absorbing pathogenic intestinal bacteria. The absorptive material is preferably also capable of absorbing diarrhea-associated viruses, intestinal toxins and gases. Suitable absorptive materials are clays such as Smectite ($Si_8Al_4O_{20}OH_4$). Other such clays are argillaceous clays. The electrolyte/sugar component contains a sodium salt, a potassium salt and a sugar. The composition is packaged in solid form and reconstituted by admixture with water prior to administration.

U.S. Pat. No. 5,192,551 discloses rehydration and infant nutrient formulas containing a neutral glycolipid, in particular, gangliotetracosylceramide. The glycolipid binds enteric virus, e.g., rotaviruses, which are pathogenic to humans. Rotaviruses are RNA viruses known to replicate in the intestinal epithelial cells of a wide range of animal species, including humans.

Electrolytes generally have a disagreeable taste. As such, rehydration solutions are often difficult to administer, especially to young children. While oral electrolyte maintenance and replenishing solutions for infants and children are available, such as Fruit-Flavored Pedialyte® manufactured by Ross Laboratories, Columbus, Ohio, there remains a need in the art for an effective rehydration formula which is readily consumed by children.

SUMMARY OF THE INVENTION

The invention is directed to a rehydration formulation and delivery system for oral administration. More particularly, the invention is directed to a frozen rehydration formulation useful in the maintenance and/or replacement of electrolytes lost during physical exercise, fatigue and/or illness. Whereas all prior art oral rehydration solutions are administered in a liquid form, the formulation of the invention is designed to be served frozen such as in the form of a popsicle or freezer pop.

The frozen formulation of the invention contains all the necessary electrolytes and levels thereof required by the Food and Drug Administration for oral rehydration formulations sold in the United States. In addition to sodium ($Na^+$), potassium ($K^+$), chloride ($Cl^-$) and citrate ions, the formulation contains a source of carbohydrate such as glucose or dextrose. Fruit flavoring and sweeteners designed to mask the unpleasant tastes of electrolytes are also provided in the rehydration formulations of the invention. Administration in the frozen form also has been discovered to lessen the offensive taste of electrolytes.

The invention provides the art with a frozen oral rehydrating composition for replacement or prevention of electrolyte loss. The composition comprises water, carbohydrate, sodium ions, potassium ions, chloride ions, and citrate ions. In a particularly preferred embodiment of the delivery system of the invention, an aliquot of rehydration solution is packaged in a freezable wrapper. Following freezing, the frozen formulation is eaten in the same way as a traditional "freezer pop". The rehydrating composition of the invention is administered in the frozen state, i.e., at a temperature of about the freezing point of said composition or colder.

The invention also provides the art with a method of replacing lost electrolytes or preventing loss of electrolytes. The method comprises orally administering to a individual in need thereof a frozen rehydrating composition comprising water, carbohydrate, sodium ions, potassium ions, chloride ions and citrate ions.

While children generally do not like to take dietary supplements and dislike the flavor thereof, the delivery system of the invention is easily administered to children. The frozen formulation is not only readily eaten by children, but aids in masking the offensive taste of electrolytes.

DETAILED DESCRIPTION OF THE INVENTION

When children are sick, the usual foods and liquids are frequently reduced or discontinued. Vomiting and diarrhea can result in further loss of essential fluids and electrolytes. In order to forestall dehydration and prevent fluid losses before serious deficits develop, replacement therapy is often required. Young children, however, dislike taking medicine, especially when it has an unpleasant taste.

A rehydration formulation and delivery system for oral administration has now been discovered which is readily and eagerly consumed by children. The oral rehydration formulation of the invention is designed to be served frozen. Following preparation of the liquid rehydrating solution, the liquid product is encapsulated within a sealable freezable packaging material and sealed such as by heat sealing. In a preferred embodiment of the invention, a single dose of rehydration solution is packaged in a hermetically sealed freezable pouch. Various types of packaging materials which can be used to practice the invention, such as that used in traditional freezer pops, would be readily apparent to the skilled artisan. The wrapping material is preferably a type which will allow markings, such as product identification, ingredients, etc., to be placed on the exterior surface thereof. The rehydration formulation is shipped and stored, preferably in multiple units thereof, in this condition. It is contemplated that multiple units or freezer pops will be packaged together for purposes of commercialization.

Prior to administration, a package of liquid rehydration solution is frozen. Following freezing, the package is opened and the contents thereof eaten. Since the frozen rehydration formulation will normally be administered at ambient temperatures, the amount of rehydration liquid contained in each package is preferably an amount which can be consumed in its entirely while still in the frozen state. Preferably 20–35 ounces, more preferably 2.0 to 2.5 ounces per package. In a particularly preferred embodiment, 2.1 ounces of sterile rehydration solution is encapsulated within an rectangular, e.g., 1"×8," freezable wrapper material. Clear plastic wrapper material is preferred.

The frozen formulation of the invention is eaten in the same way as a traditional freezer pop. While the invention will hereinafter be described in terms of a rehydrating freezer pop, it is to be understood that other packaging systems for the delivery of frozen rehydration formulations are also encompassed by the invention and are within the scope thereof.

The rehydrating freezer pop provides, in a convenient dosage form, a balanced formula of important electrolytes for the effective maintenance and replacement of fluid deficits. This formulation is especially advantageous for children reluctant to drink or who vomit frequently. The rehydrating freezer pops of the invention are convenient, nonthreatening, painless, and easy to administer to young children.

The rehydrating freezer pop of the invention is advantageously used to supply water and electrolytes needed for the maintenance and/or replacement of mild to moderate losses of electrolytes as in diarrhea or vomiting during illnesses. Such a formulation also provides a useful way of coaxing sick children, such as those in a post-operative recovery period, into taking necessary replenishing fluids. Children prefer to eat a freezer pop than drink a cup of medicine. The rehydrating freezer pops also helps reduce a fever and soothe a sore throat. The rehydrating freezer pops, may also be used to ease discomfort and nausea following cancer chemotherapy.

In addition to being a useful therapeutic agent, the rehydrating freezer pop of the invention is a particularly useful prophylactically. Ingestion of a frozen rehydration pop helps maintain proper electrolyte balance and avoid dehydration. The rehydrating freezer pops of the invention are particularly useful for administration to women during labor and childbirth, being easier to consume than conventionally made ice chips and providing electrolytes lacking therein. Rehydrating freezer pops may be administered to energetic youngsters to avoid fluid imbalances resulting from the expenditure of energy during normal day-to-day activities, as well as following physical exertion and exercise. The rehydrating freezer pops help maximize rehydration by quickly delivering essential fluids and electrolytes. The rehydration freezer pop provides a healthy, energizing, thirst quenching snack which is appealing to very young children, as well as older children and adults.

The frozen rehydrating pop of the invention is made by first preparing a solution of potassium, sodium, chloride and a base in water. Suitable bases include acetate, lactate, citrate and/or bicarbonate. Sodium chloride, potassium citrate, sodium citrate, and potassium chloride are suitable sources of electrolytes. Citric acid may also be used. For the prevention of dehydration or maintenance of hydration, sodium ion may be added at a concentration of 20–100 mEq/L, typically a level of from 40–60 mEq/L is sufficient. Preferred potassium levels are from 20–30 mEq/L with a broad range of 10–100 mEq/L being operable. The chloride anion is preferably added at 30–80 mEq/L with a broad range of 25–100 mEq/L being operable. The base, which is selected from the group consisting of acetate, lactate, citrate or bicarbonate, is preferably added at a range of 25–40 mEq/L with a broad range of 20–50 mEq/L being operable. A preferred rehydration formula for use in the invention comprises 45 mEq (1022 mg) of $Na^+$, 20 mEq (784 mg) of $K^+$, 35 mEq (1232 mg) of $Cl^-$ and 30 mEq (1918 mg) citrate ions per liter. This formulation provides all electrolytes at levels required by the Food and Drug Administration for oral rehydration formulations sold in the United States.

The frozen rehydration formulation also contains a carbohydrate component. Any carbohydrate used in prior art oral rehydration solutions may be used to practice the present invention. Suitable sugars include glucose, fructose and polymers thereof including corn syrup, high fructose corn syrup, sucrose, maltodextrin and combinations thereof. Glucose, for example, not only helps to promote sodium and water absorption but provides energy. A preferred carbohydrate source is a mixture of crystalline fructose, sucrose and dextrose. The amount of carbohydrate depends on the selection thereof and is readily determinable by the skilled artisan.

The rehydration formula for use in the claimed invention also, preferably, contains flavoring and/or sweetening agents. While individual perception of flavoring agents and sweetening agents depend on the interrelationship of many factors, flavors and sweeteners may also be perceived separately. Thus, as is well known in the art, flavor and sweetener perception may be both dependent upon each other and independent of each other. For example, when a large amount of flavoring agent is used, a small amount of sweetening agent may be readily perceptible and vice versa. In general, the flavor and sweetener is used in an amount effective to provide a desired taste. Such amounts will vary with the flavor and sweetener selected. The exact range of amounts for each type of sweetener and/or flavoring is known in the art and/or is readily determinable by the skilled artisan.

Flavoring agents useful to prepare the rehydration formula of the invention include those flavorings known to the skilled artisan such as flavorings derived from plants, leaves, flowers, fruits, and the like, and mixtures thereof. Representative flavor oils include cinnamon oil and oil of wintergreen (methyl salicylate). Useful flavorants include artificial, natural and synthetic fruit flavors such as citrus oils, including lemon, lime, orange, grape, and grapefruit, and fruit essences including apple, strawberry, raspberry, cherry, pineapple, tropical and the like, and mixtures thereof. Natural flavorings are preferred for use in the practice of this invention. Particular preferred flavors are orange, grape and cherry.

The sweetening agent used may be selected from a wide range of materials including water-soluble sweeteners, water-soluble artificial sweeteners, water-soluble sweeteners derived from naturally occurring water-soluble sweeteners, and mixtures thereof. Without being limited to particular sweeteners, representative categories and examples include:

(a) water-soluble sweetening agents such as monosaccharides, disaccharides and polysaccharides such as monosaccharides, disaccharides and polysaccharides such as xylose, ribulose, glucose (dextrose), mannose, galactose, fructose (levulose), sucrose (table sugar), maltose, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydrogenated starch hydrolysates and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like; and (c) water-soluble sweeteners derived from naturally occurring water-soluble sweeteners, such as chlorinated derivatives of ordinary sugar (sucrose), known, for example, under the product designation of Sucralose.

Preferred sugar based-sweeteners are sugar (sucrose), corn syrup and mixtures thereof. Preferred sugarless sweeteners are sugar alcohols. Preferred sugar alcohols are selected from the group consisting of sorbitol, xylitol, maltitol, mannitol, and mixtures thereof. More preferably, sorbitol or a mixture of sorbitol and mannitol is utilized.

While in a preferred embodiment, no coloring agent is used, a coloring agent, if desired, can be used in an amount effective to produce the desired color. Coloring agents include pigments such as titanium dioxide. Particularly useful colorants include water-soluble natural food colors and dyes suitable for food, drug and cosmetic applications. These colorants are known as F.D. & C. dyes and lakes. Illustrative nonlimiting examples include the indigoid dye known as F.D. & C. Blue No. 2, which is the disodium salt of 5,5-indigotindisulfonic acid. Similarly, the dye known as F.D. & C. Green No. 1 comprises a triphenyl-methane dye and is the monosodium salt of 4-[4-(N-ethyl-p-sulfoniumbenzylamine) diphenylmethylene]-[1-(N-ethyl-N-p-sulfoniumbenzyl)-delta-2,5-cycohexadieneimine]. A full recitation of all F.D. & C. colorants and their corresponding chemical structures may be found in the Kirk-Othmer Encyclopedia of Chemical Technology, 3rd Edition, Volume 5, pages 857–884.

The rehydrating composition may also contain various pharmacological agents such as, for example, an antibiotic. If desired, the rehydrating composition may also contain bioavailable minerals, anabolic nutrients, antioxidants, vitamins, and/or suspending agents. Examples of anabolic nutrients include vanodyl sulfate, alphaketoglutarate, inosine. Examples of antioxidants include carotenoids, ascorbic acid and salts thereof, tocopherols, reduced glutathione and coenzyme Q10. As referred to herein, bioavailable minerals include inorganic substances, metals, and the like, required in the human diet. Suitable minerals include manganese, chromium, calcium, iron, zinc, selenium, copper, iodine, magnesium, phosphorus, and the like such as magnesium oxide, calcium carbonate, ferrous sulfate, ferrous fumarate, zinc chloride, cupric chloride, calcium iodate; and mixtures thereof. Such minerals may be present as amino acid chelates. An amino acid chelate is defined in the food art as a metal ion from a soluble salt with an amino acid or peptide ligand with a mole ratio of one mole of metal to one to three, preferably two, moles of amino acids to form coordinate covalent bonds.

The term vitamin, as used herein, refers to trace organic substances that are required in the diet and include, without limitation, thiamin, riboflavin, nicotinic acid, pantothenic acid, pyridoxine, biotin, folic acid, vitamin $B_{12}$, lipoic acid, ascorbic acid, vitamin A, vitamin D, vitamin E and vitamin K. Also included with the term vitamin are the coenzymes thereof. Coenzymes are specific chemical forms of vitamins. Coenzymes include thiamine pyrophosphates (TPP), flavin mononucleotide (FMM), flavin adenine dinucleotide (FAD), nicotinamide adenine dinucleotide (AND), nicotinamide adenine dinucleotide phosphate (NADP) Coenzyme A (CoA) pyridoxal phosphate, biocytin, tetrahydrofolic acid, coenzyme $B_{12}$, lipolysine, 11-cis-retinal, and 1,25-dihydroxycholecalciferol. The term vitamin also includes choline, carnitine, and alpha, beta, and gamma carotenes.

The suspending agent may be, for example, a hydrocolloid (such as sodium carboxymethylcellulose, xanthan gum, hydroxypropylmethyl cellulose, polyethylene glycol, a dextrin, gum karaya, gum tragacanth, gum acacia, gum guar or a polysaccharide), a polyol (such as glycerin, propylene glycol or sorbitol) or a surfactant (such as dioctyl sulfosuccinate, polysorbate-40 or sorbitan monooleate).

While the frozen rehydration formulation of the invention desirably contains no artificial flavors or colors, it is to be understood that the use of artificial flavoring and/or coloring agents is encompassed within the scope of the claimed invention.

EXAMPLE

Oral rehydration solution is formulated and manufactured on a production scale using the following procedure for a 2000 gallon batch.

1800 gallons of deionized water is heated to a temperature of about 50°–60° C. are first pumped into a blending tank. Then the dry ingredients, sodium chloride, potassium citrate, sodium citrate and dextrose, are added to the water through a Tri-Blender. After the dry ingredients are added 21.2 kg of Natural Cherry Flavor liquid is added to the product in the blending tank. The blended product is then pumped through a cooler at a temperature of about 5°–10° C. The product is then standardized by adding 200 gallons of purified water. The dry ingredients are added in an amount to provide a final standardized product containing 45 mEq of sodium, 20 mEq of potassium, 35 mEq of chloride, 30 mEq of citrate and 25 g of dextrose per liter of product. The liquid product is filled into containers for sterilization. Following sterilization, the liquid is packaged for storage and shipment.

While sterilization can be accomplished before packaging, sterilization of the liquid product can also be conveniently accomplished following the packaging thereof. Sterilization can be accomplished by any of the methods known in the art. The sterile prepackaged formulation is ready to use. No mixing or dilution is necessary. Moreover, the unitary dosages provided by the invention is more economical because there is less product waste. Unlike prior art oral rehydration products, which must be discarded 48 hours after opening or mixing, unopened pops can be stored at room temperature or in the freezer for future use. In use, individual packages are frozen, opened and eaten.

It is to be understood that various changes in the details, materials and arrangements of parts which have been herein described and illustrated in order to explain the nature of the invention, may be made by those skilled in the art within the principle and scope of the invention as expressed in the appended claims.

We claim:

1. A method for providing electrolytes to a child in need of electrolyte replacement comprising:

(a) providing a rehydrating composition comprising:
aqueous solution of about 45 m Eq of sodium ion, about 20 m Eq of potassium ion, and about 35 m Eq of chloride ion per liter of water and a water soluble natural carbohydrate wherein the rehydrating composition is sealed in freezable packing materials;

(b) freezing the rehydrating composition; and (c) opening the freezable packaging material and orally administering the frozen rehydrating composition to the child.

2. A method according to claim 1, wherein there is about 2.1 ounces of frozen rehydrating composition sealed in the freezable packaging material.

3. The method of claim 1 wherein the carbohydrate is selected from the group consisting of xylose, ribulose, dextrose, glucose, mannose, galactose, fructose, sucrose, maltose and mixtures thereof in an amount of about 25 grams per liter.

4. A method for providing electrolytes to a child in need of electrolyte replacement comprising:

(a) providing a rehydrating composition comprising:
an aqueous solution of about 45 m Eq of sodium ion, about 20 m Eq of potassium ion, and about 35 m Eq of chloride ion per liter of water and a water soluble carbohydrate selected from the group consisting of xylose, ribulose, dextrose, glucose, mannose, galactose, fructose, sucrose, maltose and mixtures thereof in an amount of about 25 grams per liter with a flavoring agent: wherein about 2.1 ounces of the rehydrating composition is sealed in freezable packing materials;

(b) freezing the rehydrating composition; and (c) opening the freezable packaging material and orally administering the frozen rehydrating composition to the child.

* * * * *